(12) United States Patent
Lambrechts et al.

(10) Patent No.: US 12,097,235 B2
(45) Date of Patent: Sep. 24, 2024

(54) ANTI-ACNE PHARMACEUTICAL COMPOSITIONS

(71) Applicant: UNIVERSITY OF PRETORIA, Hillcrest (ZA)

(72) Inventors: Isa Anina Lambrechts, Pretoria Noth (ZA); Namrita Lall, Pretoria (ZA)

(73) Assignee: UNIVERSITY OF PRETORIA, Hillcrest (ZA)

( * ) Notice: Subject to any disclaimer, the term of this patent is extended or adjusted under 35 U.S.C. 154(b) by 565 days.

(21) Appl. No.: 17/312,608

(22) PCT Filed: Dec. 10, 2019

(86) PCT No.: PCT/IB2019/060604
§ 371 (c)(1),
(2) Date: Jun. 10, 2021

(87) PCT Pub. No.: WO2020/121187
PCT Pub. Date: Jun. 18, 2020

(65) Prior Publication Data
US 2023/0181664 A1 Jun. 15, 2023

(30) Foreign Application Priority Data
Dec. 10, 2018 (ZA) .................. 2018/08307

(51) Int. Cl.
| | | |
|---|---|---|
| *A61K 36/53* | (2006.01) | |
| *A61K 9/06* | (2006.01) | |
| *A61K 31/352* | (2006.01) | |
| *A61K 47/10* | (2017.01) | |
| *A61K 47/14* | (2017.01) | |
| *A61K 47/18* | (2017.01) | |
| *A61K 47/32* | (2006.01) | |
| *A61P 17/10* | (2006.01) | |

(52) U.S. Cl.
CPC ............ *A61K 36/53* (2013.01); *A61K 9/06* (2013.01); *A61K 31/352* (2013.01); *A61K 47/10* (2013.01); *A61K 47/14* (2013.01); *A61K 47/18* (2013.01); *A61K 47/183* (2013.01); *A61K 47/32* (2013.01); *A61P 17/10* (2018.01); *A61K 2236/331* (2013.01); *A61K 2236/333* (2013.01)

(58) Field of Classification Search
None
See application file for complete search history.

(56) References Cited

U.S. PATENT DOCUMENTS

2015/0079202 A1    3/2015   Chen et al.

FOREIGN PATENT DOCUMENTS

JP         2017071573 A       4/2017

OTHER PUBLICATIONS

International Search Report and Written Opinion issued on Mar. 18, 2020 for corresponding PCT Application No. PCT/IB2019/060604.
Patricia Rijo et al., "Antimicrobial Plant Extracts Encapsulated into Polymeric Beads for Potential Application on the Skin", Polymers, vol. 6, No. 2, 2014, pp. 479-490 XP055673661.
Renata Kubinova et al., "Antimicrobial and enzyme inhibitory activities of the constituents of Plectranthus madagascariensis (Pers.) Benth", Journal of Enzyme Inhibition and Medicinal Chemistry, vol. 29, No. 5, 2014, pp. 749-752 XP055673463.
Wellsow, J. et al., "Insect-antifeedant and antibacterial activity of diterpenoids from species of *Plectranthus*", Phytochemistry, Pergamon Press, GB, vol. 67, No. 16, 2006, pp. 1818-1825 XP028059846.
Lambrechts, I. A. et al., "Potential of Lamiaceae-plants for acne vulgaris and skin hyperpigmentation", South African Journal of Botany, 2015, vol. 98, 2015, p. 184 XP009519141.
Lukhoba, C. W. et al., "Plectranthus: A review of ethnobotanical uses", Journal of Ethnopharmacology, Elsevier Ireland Ltd, IE, vol. 103, No. 1, 2006, pp. 1-24 XP027939509.
Wen-Cheng Huang et al., "Inhibitory effects of wild bitter melon leaf extract on Propionibacterium acnes-induced skin inflammation in mice and cytokine production in vitro", Food & Function, vol. 6, No. 8, 2015, pp. 2550-2560 XP055672690.

*Primary Examiner* — Robert A Wax
*Assistant Examiner* — Quanglong N Truong
(74) *Attorney, Agent, or Firm* — POLSINELLI PC

(57) ABSTRACT

The invention provides a pharmaceutical composition suitable for topical application. The pharmaceutical composition comprises an extract of Plectranthus aliciae and a pharmaceutically acceptable carrier. The invention extends to provide a pharmaceutical composition for the treatment of acne, a pharmaceutical gel composition, a substance or composition comprising an extract of Plectranthus aliciae, a use of a Plectranthus aliciae extract, and various methods of preventing or treating acne.

20 Claims, 3 Drawing Sheets

**%Yield, antibacterial, antioxidant activity and cytotoxicity of *Plectranthus aliciae*.**

*Positive controls: Antibacterial - Tetracycline, Antioxidant - Vitamin C & Cytotoxicity - Actinomycin D.*

|  | Plant % yield | Biofilm inhibition (µg/ml) | AI-2 (µg/ml) | Antioxidant IC$_{50}$±SD (µg/ml) | | Cytotoxicity IC$_{50}$±SD (µg/ml) | |
|---|---|---|---|---|---|---|---|
|  |  |  |  | DPPH | NO | HaCat | B16-F10 |
| *P. aliciae* | 12.31 | 28.5±3.4 | 32.3±13.1 | 4.8±2.6 | 177.9±5.2 | 101.8±2.8 | 82.2±1.5 |
| Positive control | - | 10.6±0.8 | 21.0±11.4 | 9.0±2.0 | 65.8±5.9 | 0.0094±0.001 | 0.7±0.5 |

Figure 1

**Antibacterial activity of *Plectranthus aliciae*, semi-pure fractions and identified pure compounds**

*NI: No inhibition at the highest concentration at 500 µg/ml*

|  | Antibacterial MIC (µg/ml) |
|---|---|
| *P. aliciae* | 31.25 |
| Hexane fraction | 7.8 |
| Ethyl acetate fraction | 15.6 |
| Luteolin | 62.5 |
| Rosmarinic acid | NI |
| Quercitrin | NI |
| Syringic acid | NI |
| Positive control: Tetracycline | 0.78 |

Figure 2

**IC$_{50}$ data of positive control (reference inhibitor) and *P. aliciae* tested for lipase inhibition.**

| Sample | Concentration | % Inhibition (Mean ± SEM) | IC$_{50}$ (95% Confidence Interval) |
|---|---|---|---|
| Orlistat (Reference inhibitor) | 10 ng/ml | 16.12 ± 1.60 | 50.73 ng/ml (40.71 - 63.30) |
| | 25 ng/ml | 34.51 ± 1.25 | |
| | 50 ng/ml | 55.06 ± 1.35 | |
| | 100 ng/ml | 67.29 ± 0.47 | |
| | 250 ng/ml | 76.36 ± 0.52 | |
| *P. aliciae* | 1 µg/ml | 2.48 ± 1.29 | 21.66 µg/ml (18.85 - 24.82) |
| | 5 µg/ml | 4.58 ± 3.29 | |
| | 10 µg/ml | 15.63 ± 1.79 | |
| | 25 µg/ml | 62.80 ± 2.02 | |
| | 50 µg/ml | 85.33 ± 0.81 | |
| | 100 µg/ml | 90.98 ± 0.64 | |
| | 250 µg/ml | 97.23 ± 0.05 | |

Figure 3

**Cyclooxygenase-2 inhibitory activity of *Plectranthus aliciae*.**

*Data is expressed as IC$_{50}$ ± Standard deviation (SD). IC$_{50}$: fifty % inhibitory concentration.*

| | IC$_{50}$ ±SD (µg/ml) |
|---|---|
| *Plectranthus aliciae* | 28.6±4.8 |
| Positive control: Ibuprofen | 0.09±0.04 |

Figure 4

**MMP-9 inhibition by *Plectranthus aliciae* ethanolic extract.**

*Data is expressed as $IC_{50}$ ± Standard deviation (SD). $IC_{50}$: fifty % inhibitory concentration.*

|  | $IC_{50}$ ±SD (µg/ml) |
|---|---|
| *Plectranthus aliciae* | 277.1±4.7 |
| Positive control: NNGH[a] | | a: 96.1 % inhibition at 1.3µM (0.411 µg/ml)

Figure 5

Average amount of colonies of *S. typhimurium* observed at the indicated concentrations of *Plectranthus aliciae*

| Concentration of test sample (mg/ml) | Number of colonies | |
|---|---|---|
| | TA 98 | TA 100 |
| 5 | 13±0.0 | 134.7±4.0 |
| 0.5 | 15±1.0 | 141.0±1.0 |
| 0.05 | 21.3±1.5 | 116.3±4.5 |
| Positive control (4-NQO) | 210±4.4±9.81 | 1064.7±1.5±9.07 |
| Blank | 20.3±0.6±3.46 | 113.3±0.6 |

Figure 6

ANTI-ACNE PHARMACEUTICAL COMPOSITIONS

CROSS-REFERENCE TO RELATED APPLICATIONS

This application is a national stage application (under 35 U.S.C. § 371) of PCT/IB2019/060604, filed Dec. 10, 2019, which claims benefit of South African Application No. 2018/08307, filed Dec. 10, 2018, which are incorporated herein by reference in their entireties.

FIELD OF THE INVENTION

This invention relates to anti-acne pharmaceutical compositions. In particular, the invention relates to a pharmaceutical composition suitable for topical application, a pharmaceutical composition, a pharmaceutical composition for the treatment of acne, a pharmaceutical gel composition, a substance or composition comprising an extract of Plectranthus aliciae, a use of a Plectranthus aliciae extract and methods of preventing or treating acne.

BACKGROUND OF THE INVENTION

Acne vulgaris (hereinafter "acne") is one of the most common chronic inflammatory diseases that affects adolescents and adults alike. In particular, this disease affects approximately 79% to 95% of adolescents, approximately 40% to 45% of people over 25 years of age, and approximately 12% of women and 3% of men at middle age. Overall, acne affects around 9.4% of the world's population, making it the $8^{th}$ most prevalent disease worldwide. Acne is known to lead to permanent scaring of the skin, as well as physiological and emotional problems (Cordain et al., 2002; Leyden, 1997).

Acne is an inflammatory disease of the pilosebaceous and occurs where these units are in high density, such as the back, face, neck, shoulders and upper chest (Williams et al., 2012). *Cutibacterium acnes* (previously known as *Propionibacterium acnes* or *P. acnes*), although part of the normal micro-flora of the skin, is a Gram-positive obligate anaerobic organism that contributes to the formation and inflammation of acne.

Current acne therapies use retinoids to suppress the cytokines that stimulate the production of nitric oxide (NO) in cells. Tetracycline, a drug considered a first line antibiotic to treat the disease, has shown to inhibit nitric oxide synthase (NOS) producing peroxynitrite in vitro and in vivo. It has been proposed that the anti-acne activity of doxycycline, a particular tetracycline, may be due to the ability of the drug to reduce the transfer of neutrophils to the inflammatory site and also reduce the inflammatory effect of cytokines and matrix metalloproteinase-9 (MMP-9). It has been further proposed that the MMP inhibitory activity of tetracycline may be due to its ability to bind metals ions, such as $Ca^{2+}$ and $Zn^{2+}$, that are vital for the enzyme to maintain its conformation and hydrolytic activity. A major drawback of current tetracycline therapies is that they have shown to cause antibiotic resistance in *C. acnes* and to contribute to photodamage of the skin (Mayur et al., 2010; Pretorius, 2010; Sarici et al., 2010). Doxycycline has also been found to cause dose dependent photosensitivity in some patients (Seftor et al., 1998; Simonart et al., 2008).

Other therapies currently used to relieve the symptoms associated with acne present further drawbacks. For example, some topical therapies prevent the formation of comedones but this type of treatment is slow and often irritating or damaging to the skin (Layton, 2005).

Recent studies have confirmed antibiotic resistance in the disease, therefore extending the treatment period. Biofilm formation has been linked to quorum sensing. Acne bacteria have the ability to release autoinducer-2 molecules (AI-2) as part of quorum sensing. The release of AI-2 could contribute to biofilm formation and virulence associated with inflammatory acne (Coenye et al., 2007).

Post inflammatory hyperpigmentation (PIH) is a sequel of inflammatory dermatoses, such as acne, which predominantly affects darker skinned people. Such PIH is characterised by skin hyperpigmentation which has physiological implications, especially for middle-aged women who are mostly affected, and the long-term management thereof is deemed a therapeutic challenge to most dermatologists (Rigopoulos et al., 2007). Studies have found that PIH worsens when affected areas are exposed to ultraviolet (UV) radiation or persistent/recurring inflammation (Davis and Callender, 2010).

Topical therapies for PIH have shown to lighten areas of hypermelanosis and consist of depigmenting agents together with a photoprotective sunscreen and topical tyrosinase inhibitors. Other therapies include laser therapy and chemical peeling. However, a major drawback of all current therapies for PIH is that such therapies can be harmful to the skin and can worsen PIH from the irritation caused by use.

The Lamiaceae family is a family of about 233 genera and 6900 species. Most of these plants are aromatic and are widely used as herbs, including basil, lavender, mint, rosemary, thyme and sage. Many genera of the Lamiaceae family, such as Lavandula, Ocimum, Rosmarinus and Salvia, are well known for their aromatic properties and are easy to cultivate.

Of the Lamiaceae family is Plectranthus aliciae (synonym: Plectranthus madagascariensis var. aliciae), a perennial ground cover plant. It is small to medium in size and is endemic to South Africa, found particularly in the Eastern Cape and KwaZulu-Natal provinces. The plant grows well in shady areas and does not need a significant amount of water to grow optimally (Solomon, 2009). Traditional uses of P. aliciae include for the treatment of cold coughs and various types of respiratory problems (Breyer-Brandwijk and Watt, 1962; Lukhoba et al., 2006; Raimondo et al., 2009).

The present invention aims to address the drawbacks of existing therapies for acne and PIH, by providing a novel composition (and associated methods) which is derived from nature, is organic and which reduces the negative side effects experienced by patients. Furthermore, the composition is simple and cost-effective to manufacture and the associated methods are simple in technique.

In this specification, reference is made to the following sources:

Breyer-Brandwijk, M. G. and Watt, J. M., 1962 The Medicinal and Poisonous Plants of Southern and Eastern Africa. 2nd Edition, E. and S. Livingstone Ltd., Edinburgh.

Cordain, L., Lindeberg, S., Hurtado, M., Hill, K., Eaton, S. B. and Brand-Miller, J., 2002. Acne vulgaris: a disease of Western civilization. Archives of Dermatology 138, 1584-1590.

Coenye, T., Peeters, E., Nelis, H. J., 2007. Biofilm formation by *Propionibacterium acnes* is associated with increased resistance to antimicrobial agents and increased production of putative virulence factors. Res. Microbiol. 158, 386-392. doi:10.1016/j.resmic.2007.02.001.

Davis, E. C. and Callender, V. D., 2010. Postinflammatory hyperpigmentation: a review of the epidemiology, clinical features, and treatment options in skin of color. The Journal of clinical and aesthetic dermatology 3, 20-31.

Fujimoto, A., Shingai, Y., Nakamura, M., Maekawa, T., Sone, Y., Masuda, T., 2010. A novel ring-expanded product with enhanced tyrosinase inhibitory activity from classical Fe-catalyzed oxidation of rosmarinic acid, a potent antioxidative Lamiaceae polyphenol.

Javanmardi, J., Khalighi, A., Kashi, A., Bais, H., Vivanco, J., 2002. Chemical characterization of basil (Ocimum basilicum L.) found in local accessions and used in traditional medicines in Iran. Journal of Agricultural and Food Chemistry 50, 5878-5883.

Kendre, G., Raghavan, R., Cheriyamundath, S. and Madassery, J., 2013. Tetracycline and Glutathione Inhibit Matrix Metalloproteinase Activity: An In Vitro Study Using Culture Supernatants of L929 and Dalton Lymphoma Cell Lines. Journal of Cancer Research, 2013.

Landa, P., Skalova, L., Bousova, I., Kutil, Z., Langhansova, L., Lou, J. D. and Vanek, T., 2014. In vitro anti-proliferative and anti-inflammatory activity of leaf and fruit extracts from Vaccinium bracteatum Thunb. Pakistan Journal of Pharmaceutical Sciences 27, 103-106.

Layton, A. M., 2005. Acne vulgaris and similar eruptions. Medicine 33, 44-48.

Leyden, J. J., 1997. Therapy for acne vulgaris. The New England Journal of Medicine 336, 1156-1162.

Lukhoba, C. W., Simmonds, M. S. and Paton, A. J., 2006. Plectranthus: A review of ethnobotanical uses. Journal of ethnopharmacology 103, 1-24.

Maron, D. M. and Ames, B. N., 1983. Revised methods for the Salmonella mutagenicity test. Mutation Research/Environmental Mutagenesis and Related Subjects, 113(3-4), 173-215.

Mavundza, E., Tshikalange, T. E., Lall, N., Hussein, A. A., Mudau, F. N., Meyer, J. J. M., 2010. Antioxidant activity and cytotoxicity effect of flavonoids isolated from Athrixia phylicoides.

Mayur, B., Sandesh, S., Shruti, S. and Sung-Yum, S., 2010. Antioxidant and α-glucosidase inhibitory properties of Carpesium abrotanoides L. Journal of Medicinal Plants Research 4, 1547-1553.

Mortelmans, K. and Zeiger, E., 2000. The Ames Salmonella/microsome mutagenicity assay. Mutation Research/Fundamental and Molecular Mechanisms of Mutagenesis, 455(1), 29-60.

Momtaz, S., Mapunya, B., Houghton, P., Edgerly, C., Hussein, A., Naidoo, S. and Lall, N., 2008. Tyrosinase inhibition by extracts and constituents of Sideroxylon inerme L. stem bark, used in South Africa for skin lightening. Journal of Ethnopharmacology 119, 507-512.

Pretorius, C., 2010. Antioxidant properties of Lippia javanica (Burm.f.) Spreng (Doctoral dissertation, North-West University).

Raimondo, D., von Staden, L., Foden, W., Victor, J. E., Helme, N. A., Turner, R. C., Kamundi, D. A. and Manyama, P. A. 2009. Red List of South African Plants. Strelitzia 25. South African National Biodiversity Institute, Pretoria.

Rigopoulos, D., Gregoriou, S. and Katsambas, A., 2007. Hyperpigmentation and melasma. Journal of cosmetic dermatology 6, 195-202.

Sarici, G., Cinar, S., Armutcu, F., Altinyazar, C., Koca, R. and Tekin, N., 2010. Oxidative stress in acne vulgaris. Journal of the European Academy of Dermatology and Venereology 24, 763-767.

Scheckel, K. A., Degner, S. C. and Romagnolo, D. F., 2008. Rosmarinic acid antagonizes activator protein-1-dependent activation of cyclooxygenase-2 expression in human cancer and nonmalignant cell lines. The Journal of Nutrition 138, 2098-2105.

Seftor, R. E., Seftor, E. A., De Larco, J. E., Kleiner, D. E., Leferson, J., Stetler-Stevenson, W. G., McNamara, T. F., Golub, L. M. and Hendrix, M. J., 1998. Chemically modified tetracyclines inhibit human melanoma cell invasion and metastasis. Clinical & Experimental Metastasis 16, 217-225.

Sharma, R., Kishore, N., Hussein, A., Lall, N., 2014. The potential of Leucosidea sericea against Propionibacterium acnes. Phytochemistry Letters 7, 124-129.

Simonart, T., Dramaix, M. and De Maertelaer, V., 2008. Efficacy of tetracyclines in the treatment of acne vulgaris: a review. British Journal of Dermatology 158, 208-216.

Solomon, L., 2009. Plectranthus Madagascariensis var. Madagascariensis. http://kumbulanursery.co.za/plants/plectranthus-madagascariensis-var-madagascariensis 2014.

Williams, H. C., Dellavalle, R. P. and Garner, S., 2012. Acne vulgaris. The Lancet 379, 361-372.

SUMMARY OF THE INVENTION

Broadly according to a first aspect of the invention there is provided a pharmaceutical composition suitable for topical application, which comprises an extract of Plectranthus aliciae; and a pharmaceutically acceptable carrier.

The pharmaceutically acceptable carrier may be selected from the group consisting of: cream, lotion, gel, ointment, oil, emulsion, serum, skin mask, face wash, toner, sunscreen, foundation or the like.

The extract of Plectranthus aliciae may be an organic solvent-based extract, a water-based extract or the like. In particular, the extract of Plectranthus aliciae may be selected from of any one of: an alcohol extract, an ethanol extract, a methanol extract, a water extract, a diethyl ether extract, a hexanol extract, an acetone extract, a propylene glycol extract, an ethyl acetate extract, a dichloromethane extract, a chloroform extract, a petrol extract or the like. Alternatively, the extract of Plectranthus aliciae may be in the form of a combination of any two or more of the aforementioned extracts, with two or more solvents being utilised for extraction. It is to be appreciated that the extract of Plectranthus aliciae may be in the form of a crude extract or a purified extract.

The pharmaceutical composition may be in the form of an anti-acne composition. The pharmaceutical composition may be in the form of an anti-post inflammatory hyperpigmentation (anti-PIH) composition.

The pharmaceutical composition may comprise at least 28 µg/ml of the extract of Plectranthus aliciae.

The pharmaceutical composition may comprise at least 31.25 µg/ml of the extract of Plectranthus aliciae.

The pharmaceutical composition may comprise between 28 µg/ml and 1000 µg/ml of the extract of Plectranthus aliciae.

In a preferred embodiment, the pharmaceutical composition may comprise approximately 600 µg/ml of the extract of Plectranthus aliciae. In this context, "approximately" refers to a range of 100 µg/ml on either side of the amount provided (i.e. give or take 100 µg/ml).

The pharmaceutical composition may be any one or more of: anti-inflammatory, anti-bacterial, anti-oxidising, anti-fungal, depigmenting, even skin tone, a non-irritant composition or the like.

The pharmaceutical composition may include any one or more of: a preservative, a surfactant, a gelling agent, a thickening agent, at least one antioxidant, water, an emulsifier, an emollient, a solubilizer, a humectant, a stabilizer, a chelating agent, at least one acidic and/or basic agent to adjust the pH of the composition, a buffer, a or the like.

The preservative may be in the form of any one or more of: glycols, urea, parabens, ethylenediaminetetraacetic acid (EDTA), tocopheryl acetate, ascorbyl palmitate, benzoic acid, benzyl alcohol, salicylic acid, methylisothiazolinone, methylparaben, propylparaben, levulinic acid, potassium sorbate, any derivatives of the aforementioned or the like.

The surfactant may be in the form of any one or more of: sodium lauryl sulfate, ammonium laureth sulfate, disodium lauryl sulfosuccinate, cocamphocarboxyglycinate, cocoamidopropyl betaine, alpha-olefin sulfonate, quaternium, steareths, any derivatives of the aforementioned or the like.

The gelling agent and/or thickening agent may be in the form of any one or more of: gum (e.g. xanthan gum), starch, agar-agar, gelatin, sodium dextran sulfate, sodium surfactin, steareth, tallow benzylmonium hectorite, carbomer, any derivatives of the aforementioned or the like.

The at least one antioxidant may be in the form of any one or more of: vitamin C, vitamin A (retinol), vitamin E, vitamin B3 (niacinamide), polyphenols, flavonoids, resveratrol, coenzyme-Q10, glutathione, any derivatives of the aforementioned or the like.

The emulsifier may be in the form of any one or more of: polysorbates, palmitates, butylene glycol, glyceryl stearate, suitable alcohols, stearic acid, polyethylene glycol (PEG), triethanolamine, ceteareth 20, any derivatives of the aforementioned or the like.

The emollient may be in the form of any one or more of: petrolatum, paraffin, mineral oil, zinc oxide, glycerin, wax, oil, butyl stearate, diglycol laurate, any derivatives of the aforementioned or the like.

The solubilizer may be in the form of any one or more of: water, alcohol, ethanol, glycol, glycerol, polyethylene glycol, propylene, povidone, any derivatives of the aforementioned or the like.

The humectant may be in the form of any one or more of: glycol, propylene glycol, glycerin, sorbitol, urea, collagen, nanolipidgel, any derivatives of the aforementioned or the like.

The chelating agent may be in the form of any one or more of: ethylenediaminetetraacetate (EDTA), tetrasodium EDTA, disodium EDTA, citric acid, any derivatives of the aforementioned or the like.

The at least one acidic and/or basic agent may be in the form of any one or more of: sodium hydroxide, citric acid, lactic acid, sodium bicarbonate, L-arginine, any derivatives of the aforementioned or the like.

The pH of the pharmaceutical composition may be in the range of 4,5 to 5,5 or any suitable pH for application to skin.

The pharmaceutical compound may further include any one or more additives selected from the group of: anti-inflammatory additives, depigmenting additives, antibacterial additives, antifungal additives, antiallergenic additives, vitamin(s), sunscreen, moisturizers, exfoliators, fragrances, colourants or the like.

The extract of Plectranthus aliciae may be prepared by an extraction method which includes the steps of:
 suspending plant material obtained from a Plectranthus aliciae plant in a solvent, to render an extraction solution;
 removing the plant material from the extraction solution, to render a filtrate; and
 removing remaining solvent from the filtrate, thereby recovering an extract of Plectranthus aliciae.

In a preferred embodiment, the plant material may be in the form of leaves. In other embodiments, the plant material may be in the form of any one or more of: stems, roots or the like.

The solvent may be selected for its affinity to an active compound of Plectranthus aliciae against acne (e.g. polarity). The solvent may be in the form of any one or combination of: alcohol, ethanol, methanol, hexanol, diethyl ether, acetone, propylene glycol, ethyl acetate, dichloromethane, chloroform, petrol, water or the like.

The extraction method may include the prior step of drying leaves of Plectranthus aliciae. In a preferred embodiment, the leaves of Plectranthus aliciae may be freeze dried for approximately one (1) week. In another embodiment, the leaves of Plectranthus aliciae may be air dried.

The extraction method may include the intermediate step of grinding the leaves of Plectranthus aliciae, the grinding being performed after drying leaves and before suspending the leaves in solvent.

The step of suspending the plant material obtained from a Plectranthus aliciae plant in a solvent may include macerating the leaves of Plectranthus aliciae in 99.9% ethanol. In a preferred embodiment, the leaves of Plectranthus aliciae may be macerated in the ethanol for about 72 hours on a shaker to form the extraction solution.

The step of removing the plant material from the extraction solution may include filtering the extraction solution to form a filtrate. In one embodiment, the extraction solution may be filtered through a Buchner funnel.

The step of removing the plant material from the extraction solution may further include subjecting the filtrate to reduced pressure. In one embodiment, the filtrate may be subjected to reduced pressure with a rotary evaporator (e.g. Rotavapor).

The step of removing remaining solvent from the filtrate may include evaporating the ethanol. In one embodiment, the ethanol may be evaporated by way of a solvent evaporator (e.g. GeneVAc EZ-2 Series Personal Evaporator).

Any one or both of the extraction solution and the filtrate may be in the form of an aqueous solution.

In use, the pharmaceutical composition may be topically applied to an area of skin affected with any one or both of acne and post inflammatory hyperpigmentation (PIH), the pharmaceutical composition reducing the appearance of acne and/or PIH. In particular, the pharmaceutical composition may be effective in reducing comedones, whiteheads, blackheads, pustules, microcysts or the like.

According to a second aspect of the invention, there is provided a pharmaceutical composition which includes
 an extract of Plectranthus aliciae in an effective amount for preventing or treating a skin condition in a subject.

The skin condition may be acne, post inflammatory hyperpigmentation (PIH), combinations of the aforementioned, or the like. The acne may be in the form of: acne vulgaris and juvenile, or the like.

The extract of Plectranthus aliciae may be derived from any one of: an organic solvent, water or the like. Specifically, the organic solvent may be ethanol.

In one embodiment, the skin condition may be acne and the pharmaceutical composition may exhibit antibacterial activity towards *Cutibacterium acnes*.

The pharmaceutical composition may also include any one or more of: a pharmaceutically acceptable carrier, a diluent, an excipient or the like. The pharmaceutically acceptable carrier may be selected from: cream, lotion, gel, ointment, oil, emulsion, serum, skin mask, face wash, toner, sunscreen, foundation or the like.

According to another aspect of the invention there is provided pharmaceutical composition for the treatment of acne which comprises at least one bioactive compound originating from a Plectranthus aliciae plant extract.

The at least one bioactive compound may be in the form of luteolin. The luteolin may constitute at least 62.5 µg/ml of the pharmaceutical composition.

According to a further aspect of the invention there is provided a pharmaceutical gel composition which comprises
an extract of Plectranthus aliciae;
at least one chelating agent;
at least one thickening agent;
at least one humectant;
at least one additional additive;
at least one basic substance to reach a predetermined pH; and
water.

The extract of Plectranthus aliciae may be in the form of an ethanolic extract. The ethanolic extract may be of approximately 10% concentration of ethanolic extract of Plectranthus aliciae. In one embodiment, the ethanolic extract may be in the form of at least 600 µg/ml of Plectranthus aliciae extract.

The at least one chelating agent may be in the form of tetrasodium ethylenediaminetetraacetate (EDTA). The tetrasodium EDTA may be of a concentration of approximately 0.1% in the pharmaceutical gel composition.

The at least one thickening agent may be in the form of carbomer. The carbomer may be of a concentration of approximately 1.12% in the pharmaceutical gel composition.

The at least one humectant may be in the form of propylene glycol. The propylene glycol may be of a concentration of approximately 2.23% in the pharmaceutical gel composition.

The at least one additional additive may include any one or more of:
diazolidinyl urea, methylparaben, propylparaben, propylene glycol or the like. In one embodiment, the at least one additional additive may include two drops of each of diazolidinyl urea, methylparaben, propylparaben and propylene glycol.

The at least one basic substance may be in the form of sodium hydroxide (NaOH). The sodium hydroxide may be added to the other substances of the pharmaceutical gel composition until the pH of the pharmaceutical gel composition reaches a pH suitable for skin. In one embodiment, the pH may be 5.5.

In one embodiment, the water may constitute approximately 96.54% of the pharmaceutical gel composition.

In one specific embodiment, the pharmaceutical gel composition may comprise: Plectranthus aliciae extract, water, tetrasodium EDTA, propylene glycol, carbomer, sodium hydroxide, diazolidinyl urea, methylparaben and propylene glycol.

The pharmaceutical gel composition may be effective in reducing any one or combination of comedones, whiteheads, blackheads, pustules, microcysts or the like.

Another aspect of the invention provides a substance or composition comprising an extract of Plectranthus aliciae for use in a method of treating and/or preventing acne in a subject.

The acne may be in the form of acne vulgaris and/or juvenile.

The subject may be human.

The substance of composition may further be used for the improvement of the appearance of PIH.

Yet a further aspect of the invention provides a use of a Plectranthus aliciae extract in the manufacturing of a medicament for treating acne.

The acne may be in the form of acne vulgaris and/or juvenile.

The medicament may be further effective for the improvement of the appearance of PIH.

The invention extends further to provide a method of treating acne, comprising: topically applying an effective amount of Plectranthus aliciae extract to a subject suffering from acne.

The invention extends yet further to provide a method of treating acne, comprising: topically applying a dose of a Plectranthus aliciae extract to a subject suffering from acne, the dose being applied at least twice daily for at least 14 consecutive days, the dose comprises between 28 µg/ml and 1000 µg/ml of the extract of Plectranthus aliciae.

In a preferred embodiment, the dose may comprise about 600 µg/ml of the extract of Plectranthus aliciae.

In one embodiment, the dose may be applied twice daily for at least 28 consecutive days.

The invention extends yet further to provide pharmaceutical composition which includes luteolin in an effective amount for preventing or treating acne. The luteolin may constitute at least 62.5 µg/ml of the pharmaceutical composition, the luteolin having a final concentration of at least 62.5 µg/ml in the pharmaceutical composition.

The acne prevented or treated may be in the form of: acne vulgaris, juvenile, or the like. The pharmaceutical composition may also be effective to reduce the appearance of post inflammatory hyperpigmentation (PIH). In some embodiments, the luteolin may be derived from a Plectranthus aliciae plant.

The invention is now described, by way of non-limiting example, with reference to the accompanying figures.

FIGURE(S)

In the figure(s):

FIG. 1 shows a table summarising the percentage yield, antibacterial activity, antioxidant activity and cytotoxicity of an ethanolic extract of Plectranthus aliciae;

FIG. 2 shows a table summarising antibacterial activity of Plectranthus aliciae, semi-pure fractions and certain identified pure compounds;

FIG. 3 shows a table summarising the $IC_{50}$ data of a positive control (reference inhibitor) and P. aliciae tested for lipase inhibition;

FIG. 4 shows a table of the cyclooxygenase-2 inhibitory activity of P. aliciae;

FIG. 5 shows a table of the matrix metalloproteinase-9 (MMP-9) inhibition by P. aliciae ethanolic extract; and FIG. 6 shows a table providing average numbers of colonies of *Salmonella typhimurium* observed at the indicated concentrations of P. aliciae.

EMBODIMENT OF THE INVENTION

1. Introduction
Plectranthus aliciae, part of the Lamiaceae family, is widely known to be aromatic but has now shown good antibacterial activity towards the acne vulgaris-causing bacteria, *Cutibacterium acnes*, with a minimum inhibitory concentration (MIC) of 31.25 µg/ml. This MIC was comparable to that of the positive control, tetracycline (0.78 µg/ml).

Noteworthy 1,1-Diphenyl-2-picrylhydrazyl (DPPH) antioxidant activity was observed for Plectranthus aliciae with a fifty percent inhibitory concentration ($IC_{50}$) of 4.8±2.6 µg/ml, whereas the positive control, vitamin C, yielded an $IC_{50}$ of 9.0±2.0 µg/ml.

The $IC_{50}$ for nitric oxide (NO) antioxidant activity was found to be 177.9±5.2 µg/ml, whilst vitamin C indicated an $IC_{50}$ of 65.8±5.9 µg/ml.

Plectranthus aliciae is considered non-toxic against B16-F10 mouse melanocytes cells ($IC_{50}$ value of 82.2±1.5 µg/ml) and against the human keratinocyte cell line (HaCat, $IC_{50}$ value of 101.8±2.8 µg/ml).

An ethanolic extract of Plectranthus aliciae was active towards enzymes associated with inflammatory acne, the inhibition of the ethanolic extract on matrix metalloproteinase-9 (MMP-9), lipase and cyclooxygenase-2 (COX-2) was determined. Plectranthus aliciae inhibited MMP-9 at an $IC_{50}$ value of 277.1±4.7 µg/ml, lipase at an $IC_{50}$ value of 13.25±15.3 µg/ml and COX-2 at an $IC_{50}$ value of 28.6±4.8 µg/ml.

Plectranthus aliciae did not display any mutagenic effects in either TA 98 or TA 100 strains of *Salmonella typhimurium* and was concluded to be non-mutagenic.

In vivo studies confirmed that the ethanolic extract is a non-irritant (0.47) when compared to a known irritant, sodium lauryl sulphate (2.01), after 72 hours.

The ethanolic extract dissolved in 40% ethanol in a gel formulation was effective in reducing comedones, whiteheads, blackheads, pustules and microcysts, as compared to a placebo, after 14 to 28 days of consecutive use.

2. Materials and Methods 2.1. Plant Collection and Preparation of Ethanolic Extract The Plectranthus aliciae plant material was collected from the Manie van der Schijff Botanical Garden in the summer of March 2014, with the help of the garden curator. A herbarium specimen of Plectranthus aliciae was deposited in the H.G.W.J. Schweickerdt Herbarium under the herbarium number 122336. After collection, the plant material was freeze dried for approximately 1 week. All plant material selected was in leaf form. The dried leaves were ground, macerated in 99.9% ethanol (~300 ml) and left on a shaker for 72 hours.

The filtrate of each plant was collected with the help of a Buchner funnel. Extracts were collected after the filtrate was subjected to reduced pressure using a Rotavapor. The ethanol was further evaporated by making use of the GeneVAc EZ-2 Series Personal Evaporator. The vials were stored at 5° C. until further use.

The percentage yield was determined as follows:

$$\% \text{ Yield} = \frac{\text{Final weight of extract}}{\text{Weight of initial plant material}} \times 100$$

2.2. Liquid-Liquid Partitioning

The ethanolic extract (16.67 g) was re-dissolved in 350 ml of distilled water. The aqueous layer extract was suspended in different solvents and successively extracted three times in hexane (3×400 ml), ethyl acetate (3×300 ml) and n-BuOH (3×400 ml). To the ethyl acetate fraction, some saline water was added to separate the aqueous layer from the solvent layer. The fractions were dried and tested for their antibacterial potential.

2.3. High-Performance Liquid Chromatography (HPLC)

The ethanolic extract was sent for HPLC analysis and the standard curves of various pure compounds determined to measure the concentration of the respective compounds in the ethanolic extract. The compounds present at the highest concentration in the ethanolic extract were tested for their anti-bacterial potential.

2.4. Antibacterial Assay

The ethanolic extract of Plectranthus aliciae was tested against *Cutibacterium acnes* (ATCC 6919). The *C. acnes* bacteria was cultured from a Kwik-Stick on mouse heart and brain agar and then incubated at 37° C. for 72 hours under anaerobic conditions before the assay was done. The 72 hour old bacterial culture was dissolved in brain heart infusion broth and the suspension was adjusted to a 0.5 McFarland standard turbidity. This led to $10^5$-$10^6$ colony forming units (CFU)/ml.

In a sterile 96-well plate, 100 µl of the samples from the stock solution that consisted of the plant extracts (2 mg/ml dissolved in 10% dimethyl sulphoxide (DMSO)) and tetracycline the positive control (0.2 mg/ml) was diluted with broth. Twofold serial dilutions were done in broth over a range to give the concentrations 500-3.9 µg/ml for the plant extract and 50-0.3 µg/ml for tetracycline. To all the wells of the 96-well plate, 100 µl of bacterial suspension was added. The solvent control wells contained 2.5% DMSO with bacterial suspension and no plant samples and the negative control, bacterial suspension with no plant samples.

The plates were incubated at 37° C. for 72 hours under anaerobic conditions. The minimum inhibitory concentration (MIC) value was determined by observing a colour change in the wells after the addition of 7-Hydroxy-3H-phenoxazin-3-one 10-oxide, also known as Resazurin or Presto Blue (Sharma et al., 2014).

To determine the inhibition of biofilm growth, a bacterial suspension with an $OD_{600}$ of 0.2 diluted 50 times was added to sterile 96-well plates together with the plant extract. The plates were incubated under anaerobic conditions at 37° C. for 3 days. The ethanolic extract of Plectranthus aliciae was tested at a starting concentration of 500 µg/ml. Tetracycline was used as the positive control and tested at a concentration starting at 50 µg/ml. Crystal violet staining was performed first by removing the supernatant broth and fixing the attached bacterial biofilm with 200 µl of 99% methanol for 15 min. The plates were left to air dry and 200 µl of crystal violet (0.5%) was added to the plates and left for 20 min where after the plates were washed with distilled water and left to air dry. Acetic acid (33%) (220 µl) was added to the plates and was left on a shaker for 15 min. The samples were then transferred to clean 96-well plates. The absorbance was measured at 590 nm with the BIO-TEK power Wave XS multi-well plate reader (A.D.P., Weltevreden Park, South Africa). The fifty percent inhibitory concentration (IC50) value was determined by using Graph Pad Prism software.

2.5. Autoinducer-2 Inhibition Assay

To a sterile 96-well plate, 40 µl of bacterial supernatant treated with the ethanolic extract was transferred to each well. A working solution of 10 mM 1,10-phenanthroline/ 3.32 mM Fe(III) pH 2, was added to each well (40 µl) and the plates were incubated for 1 minute to develop to full colour. To each well, 120 µl of distilled water was added and the plates spun down at 14 000 rpm for 5 minutes. The absorbance was measured at 510 nm using a UVNis spectrophotometer.

2.6. DPPH Radical Scavenging Assay

The antioxidant activities of Plectranthus aliciae ethanolic extract was investigated using 1,1-Diphenyl-2-picrylhydrazyl (DPPH) free radical scavenging assay as described by Mavundza (Mavundza, 2010).

To the top wells of a 96-well ELISA plate 200 µl of distilled water was added and to the remaining wells 110 µl of distilled water as a medium. Twenty microliters of plant extract and the controls was added to the first top wells that followed a double dilution. To each of the wells 90 µl of 90 µM DPPH ethanolic solution was added and left to incubate covered with aluminium foil for 30 minutes at room temperature. The final concentrations for the Plectranthus aliciae ethanolic extracts ranged from 3.9 to 500 µg/ml (Mavundza, 2010).

L-ascorbic acid (Vitamin C) at a concentration of 100 µg/ml, was used as the positive control and ethanol as the negative control, with distilled water as the blank. The radical scavenging capacities of the extracts were determined by using a BIO-TEK Power Wave Multiwell plate reader (A.D.P., Weltevreden Park, South Africa) at 515 nm using KC Junior software (Highland Park, Winooski, Vermont, USA) to measure the disappearance of DPPH at 515 nm.

The radical scavenging activity was determined as a percentage DPPH radical-scavenging that was calculated by the following equation, where AC is the absorbance of the control solution that only contains DPPH and AS is the absorbance of the plant sample in DPPH solution:

$$\% \text{ DPPH radical-scavenging} = (AC-AS)/AC \times 100$$

From these results, the fifty percent inhibitory concentration ($IC_{50}$) was determined (Mavundza, 2010). The $IC_{50}$ value was determined using GraphPad Prism software (Version 4 Graph Pad Software, San Diego, CA, USA) together with Windows Excel 2000.

2.7. NO Antioxidant Assay

The nitric oxide (NO) scavenging activity of the Plectranthus aliciae ethanolic extract was measured according to the method described by Mayur et al. (2010).

For the plant extracts in the top row of a 96-well plate, 20 µl of distilled water and 80 µl of extract was added and the samples were double diluted to a final concentration ranging from 2000 µg/ml to 15.6 µg/ml. A solution of 10 mM sodium nitroprusside (50 µl) was added to all the wells and incubated at room temperature under light for 90 minutes. Griess-llosysy's nitrite reagent (100 µl) was added to the test wells.

To the wells of the colour control, 100 µl of distilled water were added. The nitrite content was measured immediately at 546 nm. L-ascorbic acid was used as the positive control. The percentage scavenging activity was calculated as described for the DPPH assay.

2.8. Lipase Inhibition

A lipase inhibition assay was carried out as per U.S. patent method US2008/0317821 A1 with modifications. In brief, the total reaction volume contained tris buffer supplemented with NaCl and CaCl2/vehicle buffer/positive control/test sample at various concentrations, de-mineralized water, lipase enzyme and substrate (4-Methyl umbelliferyloleate). The plate was mixed and the change in fluorescence was determined at an excitation of 360 nm and emission of 460 nm using FLUOstar Optima (BMG Labtech, Germany). The positive control (reference inhibitor) used in the assay was orlistat. A control reaction was run without the test sample. The mean of the relative fluorescence unit (RFU) of all samples tested was calculated.

From the mean values, percentage inhibition (% I) of samples were calculated using the equation:

$$\% \ I = (\text{RFU of Control} - \text{RFU of Sample})/(\text{RFU of Control}) \times 100$$

The $IC_{50}$ was calculated by log probit analysis.

2.9. Cytotoxicity

2.9.1. Cell Culture

Mouse melanoma cells B16-F10 were cultured in complete Minimal Essential Eagle's Medium (MEM) containing 10% foetal bovine serum, 1.5 g/l NaHCO3, 10 µg/ml penicillin, 2 mM L-glutamine, 0.25 µg/ml fungi zone and 10 µg/ml streptomycin. The cultures were kept in a humidified atmosphere at 37° C. with 5% $CO_2$. Every third to fourth day the cells were subcultured in a ratio of 1:3 (Momtaz et al., 2008).

2.9.2. Cell Counting

In a trypan blue solution, the cells were suspended in a 1:10 dilution (10 µl of cells in 90 µl of trypan blue solution). In the chambers of a hemacytometer, about 10 µl of this mixture was loaded, where after the cells were counted with a hand-held tally under a microscope.

The concentration of cells per ml was calculated as follows (Momtaz et al., 2008);

$$\text{Cell no. (cell suspension)} = \text{Cell concentration} \times \text{Volume of cell suspended}$$

$$\text{Volume of cell suspension} = \frac{\text{Cell concentration wanted} \times \text{Volume wanted}}{\text{Concentration of cells in suspension}}$$

For example:

$$\text{Cell number (cell suspension)} =$$
$$150 \text{ cells counted} \times 10 \times 10000 = 1500000 \ \frac{\text{cells}}{\text{ml}}$$

2.9.3. Cytotoxicity Test

In the wells of a 96-well plate, about 100 000 cells were plated in triplicate. To each of the wells 100 µl of the samples dilutions were added. The dilutions for the plant sample were done by dissolving 2 mg of plant extract in 100 µl of DMSO and diluting the sample in medium to make the final concentrations of 400, 200, 100, 50, 25, 12.5, 6.25 and 3.13 µg/ml.

The negative control was DMSO and the positive control Actinomycin D that was tested at low concentrations. Actinomycin D was tested at a highest concentration of 0.5 µg/ml. A reference plate was prepared that contained the medium and sample with no cells, this was done in duplicate. The plates were incubated for 72 hours at 37° C. in 5% $CO_2$, humidified atmosphere (Momtaz et al., 2008).

After incubation, 50 µl of 57XTT reagent (1 mg/ml XTT with 0.383 mg/ml PMS) was added to cells and further incubated for 3 hours. This resulted in a colour change and the optical densities were determined at a wavelength of 450 nm with the BIO-TEK power Wave XS multi-well plate reader (A.D.P., Weltevreden Park, South Africa). The concentration at which 50% of the cells were killed ($IC_{50}$) value was calculated by using Graph Pad Prism software. Cell viability was determined by comparing the optical densities of samples with those of the negative control (Momtaz et al., 2008).

2.10. Cyclooxygenase Inhibition Assay

The assay was performed according to a procedure described by Landa et al. (2014) with human recombinant COX-2. The COX-2 (0.5 unit/reaction) was mixed with 100 mM TRIS buffer with a pH of 8.0 (180 µl) and a cofactor solution of 18 mM L-epinephrine, 5 µM porcine hematin and 50 µM $Na_2EDTA$. The plant samples that were dissolved in DMSO (10 µL) or pure DMSO (in the case of blank wells) were added to the wells of the 96-well plate. The plate was then incubated for 5 minutes at room temperature and the reaction initiated with the addition of 10 µM arachidonic acid (5 µl) incubated at 37° C. for 20 min. The reaction was stopped with the addition of 10 µl of 10% formic acid. The samples were diluted 1:15 and the PGE2 quantification achieved by the PGE2 ELISA kit. The absorbance was measured using a BIO-TEK Power Wave Multiwell plate reader (A.D.P., Weltevreden Park, South Africa) at 515 nm using KC Junior software (Highland Park, Winooski, Vermont, USA).

2.11. Matrix Metalloproteinase-9 Assay

The MMP-9 Colorimetric Drug Discovery Kit (BML-AK410) from Enzo Life Sciences was used. The experiment was carried out as described in the instruction manual. The MMP chromogenic substrate (Ac-PLG-[2-mercapto-4-methyl-pentanoyl]-LG-OC2H5) and the inhibitor N-Isobutyl-N-(4-methoxyphenylsulfonyl)glycyl hydroxamic acid (NNGH) was thawed to room temperature. The inhibitor was diluted 1/200 in assay buffer (50 mM HEPES, 10 mM CaCl2, 0.05% Brij-35, 1 mM DTNB, pH 7.5) and warmed until 37° C. The substrate was diluted 1/25 in assay buffer to the required volume. The MMP-9 enzyme was diluted in assay buffer to 1/60 and warmed until 37° C. just before the assay. The plant extract was dissolved in dimethyl sulfoxide (DMSO) to a starting concentration of 2 mg/ml.

In the plant extract wells, 50 µl of plant extract and 90 µl of buffer was added to the first well of the 96 well plate (½ volume). To the rest of the plant extract wells, 70 µl of buffer was added and the plant extracts serially diluted. Assay buffer was plated in the rest of the relevant wells as follows: blank 90 µl, control 70 µl, and NNGH 50 µl. The microplate was then incubated and allowed to equilibrate to the assay temperature (37° C.). The diluted MMP-9 enzyme (20 µl) was then added to the control, NNGH and plant extract wells. To the NNGH inhibitor wells, 20 µl of NNGH inhibitor was added. The plate was then incubated for 45 minutes at 37° C. The reaction was started with the addition of 10 µl of the diluted substrate. The plates were continuously read at $A_{412nm}$ by using a BIO-TEK Power Wave Multiwell plate reader (A.D.P., Weltevreden Park, South Africa) at one (1) minute intervals for twenty (20) minutes using KC Junior software (Highland Park, Winooski, Vermont, USA).

2.12. Mutagenicity

The Salmonella microsome assay according to Maron and Ames (1983) and modified by Mortelmans and Zeiger (2000) was used to determine the genotoxicity of selected extracts. Two *Salmonella typhimurium* tester strains, TA98 and TA100, were used for the assay, which was done without metabolic activation. Briefly, stock bacterial cultures (100 µl) incubated in nutrient broth No. 2 at 37° C. for 16 h were added (100 µl) to test samples (100 µl) followed by 500 µl of phosphate buffer saline and 2 ml of top agar (2 ml) containing biotin/histidine (0.5 mM). A positive control, 4-nitroquinoline-1-oxide (4-NQO) at a concentration of 2 µg/ml was used, and two negative controls, sterile distilled water and 10% DMSO, were also used. The mixture was vortexed, and poured on minimal agar plates and incubated for 48 h at 37° C. All samples were tested in triplicate. The absence or presence of toxicity was examined by observing the background bacterial growth.

The mutagenicity of the plant extract was determined according to the assay of Maron and Ames (1983) with slight modifications as by Mortelmans and Zeiger (2000). Two *Salmonella typhimurium* tester strains, TA98 and TA100, were used for the assay, which was done without metabolic activation. Stock bacterial cultures incubated in nutrient broth No. 2 at 37° C. for 16 h were added (100 µl) to the test sample (100 µl) followed by 500 µl of phosphate buffer saline and 2 ml of top agar (2 ml) containing biotin/histidine (0.5 mM). Here 4-Nitroquinoline-1-oxide (4-NQO) was used as the positive control at a concentration of 2 µg/ml, and two negative controls, 10% DMSO and sterile distilled water, were also used. After preparation, the samples were poured on minimal agar plates and incubated for 48 h at 37° C. The absence or presence of toxicity was examined by observing the background bacterial growth. All samples were tested in triplicate.

2.13. In Vivo Skin Irritancy Patch Test

Twenty adult female volunteers were used, of whom five had sensitive skin. Signed consent forms were obtained from all subjects. Controls and products were applied to the inner forearm of each volunteer in a randomized blinded pattern at zero hours and repeated on the same position at 24 hours. Product(s) were tested by using specially designed aluminium Finn Chambers on Scanpore® tape for occluded sites or modified Hilltop chambers for un-occluded sites. Products were tested neat.

The test sites were observed at 0 and 24 hours after application. Test sites were covered with the chambers for the first 2×23 hours, thereafter the chambers were removed. The protocol uses 1% sodium lauryl sulphate (SLS) solution as a positive control and de-ionised water as a negative control. Colour assessments were performed in a "double blind" manner in 2 ways: visual score and an instrumental score using the Minolta Cr400 Chromameter using the a* value, which measures colour on the red/green axis.

2.14. In Vivo Anti-Acne Clinical Studies

*Plectranthus aliciae* (300 mg/ml) dissolved in 40% ethanol was formulated at 10% in a gel formulation. Acne clinical studies were conducted as follows. A group of twenty-four (24) subjects between the ages of 19 to 39 were included and completed the full study. The subjects complied with the rules and specifications of the study and all results recorded were used in the noted calculations. The procedure of testing was explained to them verbally and with the consent form and medical history were signed by each subject. Personal details and each subject's assessment of their own skin type were recorded. Colour photographs were taken at each time interval to serve as a recording of the study conducted.

All subjects were instructed to rest for twenty (20) minutes before any testing was conducted. The designated left or right side of the face was cleansed with a standard eye make-up remover and allowed to air dry for three (3) minutes. The temperature and relative humidity were recorded during the time of the study. The test sites were demarcated as per test sequence substance. Two (2) trained evaluators performed a physical count on both test sites and recorded the scores. An operator trained the test subjects in applying the test products evenly to the test sites, twice a day. Subjects were restricted from using any topical products or any medication not approved by the study sponsor for the duration of the study. Subjects returned to the testing facility on fourteen (D14) and twenty-eight (D28) days respectively after baseline readings. The temperature and relative humidity were recorded during the time of the study. The primary objective sensory evaluation results were scored and rated by two (2) trained evaluators. Both inflammatory and retentional elements of acne were counted.

Objective:

The objective of the study was to determine the Acne Reduction efficacy of a test product on the face of human subjects.

Materials:

Standard Eye Make-up Remover; Sterile Cotton makeup remover pads, White Facial Tissue; and Alcohol swabs.

Camera:

VISIO FACE

Testing Conditions:

The study was carried out at an average ambient range temperature 20.5° C. to 22.8° C. with a relative humidity of 41.0% RH and 46.7% RH.

Method:

A group of twenty-four (24) subjects between the ages of 19 to 39 were included and completed the full study. A couple of deviations were observed during the study).

The subjects complied with the rules and specifications of the study and all results recorded were used in the noted calculations.

The procedure of testing was explained to them verbally and with the consent form and medical history were signed by each subject. Personal details and each subject's assessment of their own skin type were recorded.

Colour photographs were taken at each time interval to serve as a recording of the study conducted.

All subjects were instructed to rest for twenty (20) minutes before any testing was conducted.

The designated left or right side of the face was cleansed with a standard eye make-up remover and allowed to air dry for three (3) minutes.

The temperature and relative humidity were recorded during the time of the study.

The test sites were demarcated as per test sequence substance.

Two (2) trained evaluators performed a physical count on both test sites and recorded the scores.

An operator trained the test subjects in applying the test products evenly to the test sites, according to the test substance sequence.

Subjects were restricted from using any topical products or any medication not approved by the study sponsor for the duration of the study.

Subjects returned to the testing facility on twenty-eight (D28) days respectively after baseline readings.

The temperature and relative humidity were recorded during the time of the study.

Research Design:

Sensory: Objective (Physical Count)

The primary objective sensory evaluation results were scored and rated by two (2) trained evaluators. Both inflammatory and retentional elements of acne were counted.

A research design can be defined as the basic plan that guides the data collection and analysis phases of the research project. It is the framework that specifies the type of information to be collected, the sources of data, and the data collection procedure. The information needed to reach the aim of the current study is based on values that represent the Acne Reduction characteristics of human subjects and can thus be classified as interval data, since the quantitative data can be represented in a quantitative manner.

Data Sampling:

A sample can be defined as a subset of the whole population which is actually investigated by a researcher and whose characteristics will be generalised to the entire population. A sampling plan can be described as a design, scheme of action or procedure that specifies how the participants are to be selected in a survey study. A distinction is made between probability and non-probability sampling. In this study use was made of a non-probability sampling method. A non-probability sampling method can be described as the selection of a population element to be part of the sample based in some part on the judgment of the researcher. The researcher only included respondents who were 19-39 years of age. A sample of convenience was used in this study.

Statistical Data Analysis Procedure

Data Analysis:

The data was captured onto Excel and converted to extended excel statistical tests in order to do the analysis. The data analysis had the following aims:

1. To first determine whether the data was distributed normally.
2. To determine whether significant differences existed between the test product and placebo regarding the Acne Reduction efficacy.

Since the sample was relatively small and consisted of a group of at least twenty-four (24) respondents, use was made of a parametric test, the (unequal or equal variances) t-test for comparison of two sets of data. The t-test is used to determine whether a given treatment had a significant effect on a population. In the case of not normally distributed data the Wilcoxon Signed Rank Sum Test was be used.

The following statistical data analysis procedures were used:

Descriptive Analysis: Descriptive statistics are primarily aimed at describing the data.

Inferential statistics: Test hypotheses about differences in populations on the basis of measurements made on samples of subjects.

Statistically significant differences between variables are indicated by a significance value p. If the value of p is equal to or less than 0.05, it gives an indication that there is a statistically significant difference, at the 5% level of confidence.

3. Results and Discussion 3.1. Identification of Pure Compounds

The following pure compounds were identified to be present in the ethanolic extract of Plectranthus aliciae: Vitexin, Isovitexin, Luteolin, Quercitrin, Vannilic acid, Syringic acid, Caffeic acid, Epicatechin, Ferulic acid, Propyl gallate, Catechin, Rosmarinic acid, Isoquesrcitrin, 4-hydroxybenzoic acid, Protocatechuic acid and Orientin. Luteolin, Quercitrin, Syringic acid and Rosmarinic acid were identified to be the major constituents in the ethanolic extract and were tested for their antibacterial potential. To the best of the inventors' knowledge, this is the first report of Luteolin, Syringic acid and Quercitrin identified to be present in the ethanolic extract of P. aliciae.

3.2. Antibacterial, DPPH Radical Scavenging and NO Antioxidant Assays, Cytotoxicity The antibacterial activity of the ethanolic extract of Plectranthus aliciae is summarized in FIG. 1. The antibacterial activity of the ethanolic extract of Plectranthus aliciae, semi-pure fractions and identified pure compounds is summarized in FIG. 2. To the best of the inventors knowledge, the antibacterial activity of P. aliciae against *C. acnes* is being reported for the first time in this embodiment. The ethanolic extract of P. aliciae inhibited bacterial growth of *C. acnes* and exhibited a noteworthy MIC value of 31.25 µg/ml, which is comparable to the MIC value of the positive control, tetracycline, with a MIC value of 0.78 µg/ml. The hexane fraction exhibited a noteworthy MIC value of 7.8 µg/ml and the pure compound Luteolin with an MIC value of 62.5 µg/ml.

Plectranthus aliciae was confirmed to inhibit biofilm formation at a fifty percent inhibitory concentration ($IC_{50}$) of 28.5±3.4 µg/ml and autoinducer-2 production at 32.3±13.1 µg/ml.

Plectranthus aliciae was confirmed to have a noteworthy general DPPH antioxidant activity indicated by an $IC_{50}$ value of 4.8±2.6 µg/ml that was significantly different from vitamin C with an $IC_{50}$ value of 9.0±2.0 µg/ml.

Moderate NO antioxidant activity was observed for the P. aliciae ethanolic extract with an $IC_{50}$ value of 177.9±5.2 µg/ml.

For an extract to be considered toxic an $IC_{50}$ value below 100 µg/ml needs to be obtained. The positive control, Actinomycin D, is known to be cytotoxic and showed a low $IC_{50}$ of 10.960±414.11 µg/ml. Plectranthus aliciae had an $IC_{50}$ of 101.8±2.8 µg/ml and is considered to be non-toxic against human keratinocyte cells (HaCat).

3.3. Lipase Inhibition

Plectranthus aliciae exhibited in vitro lipase inhibitory activity in a dose dependent manner in the concentration range tested. Specifically, P. aliciae inhibited in vitro lipase activity with an $IC_{50}$ of 21.66 µg/ml, as shown in FIG. 3.

3.4. Cyclooxygenase-2 Inhibition

Plectranthus aliciae inhibited the COX-2 enzyme at an $IC_{50}$ of 28.6±4.6 µg/ml compared to the positive control Ibuprofen with an $IC_{50}$ at 0.09±0.04 µg/ml (see FIG. 4).

Previous studies done by Scheckel et al., (2008) reported that rosmarinic acid at 3.6 µg/ml reduced COX-2 protein levels in HT-29 cells to levels comparable to that of the control cells. The noteworthy COX-2 inhibitory activity of P. aliciae observed in the present study could be due to rosmarinic acid that known to be present in species of the Lamiaceae family. Rosmarinic acid has been reported to have anti-inflammatory activity that is comparable to Ibuprofen (Javanmardi et al., 2002).

3.5. Matrix Metalloproteinase-9 Inhibition

Referring specifically to FIG. 5, Plectranthus aliciae was found to moderately inhibit the MMP-9 enzyme. The positive control was only tested at one concentration and inhibited MMP-9 by 96% at a concentration of 0.411 µg/ml. The positive control was used as a reference to verify if the assay was successful.

No previous studies have evaluated the MMP-9 inhibition activity of P. aliciae. The results obtained in the current study are comparable to the MMP-9 inhibition activity seen for tetracycline. Previous studies done by Kendre et al. (2013) found tetracycline to inhibit 38.91% of the MMP-9 enzyme at a concentration of 100 µg/ml. The moderate activity seen for P. aliciae on the MMP-9 enzyme could be similar to the mechanism at which tetracycline inhibits the enzyme. Plectranthus aliciae is known to contain a high concentration of rosmarinic acid that has the ability to oxidise iron and could, therefore, disrupt the conformation and hydrolytic activity of the enzyme (Fujimoto et al., 2010).

3.6. Mutagenicity

The ethanolic extract of P. aliciae was applied to two different strains of bacteria according to the number of colonies. According to the results obtained, P. aliciae did not display any mutagenic effects in either TA 98 or TA 100 strains of *S. typhimurium* (see FIG. 6). Plectranthus aliciae did not display a ratio of 2 or higher in terms of revertants. The number of colonies observed may have been affected by the possibility that P. aliciae has anti-bacterial properties.

3.7. In Vivo Skin Irritancy Patch Test and Anti-Acne Clinical Studies

Results:

Descriptive Analysis:

Descriptive Analysis entails the ordering and summarising of data by means of tabulation and the calculation of descriptive measures.

Interferential Statistics:

Statistical Inference draws conclusions about the population from which the sample was drawn by using descriptive measures that has been calculated.

TABLE A

Comparison of objective sensory (physical count, PUSTULES) values for P. aliciae in a gel (FCAG014/5936) compared to the placebo gel (FCAG014/5937) test sites: Mean (±Standard Deviation)

| Time Interval | FCAG014/ 5936 | Table Ref. | FCAG014/ 5937 | Table Ref. | (Diff) p-Value | Table Ref. |
|---|---|---|---|---|---|---|
| BASELINE | 0.08 (±0.35) | F1 | 0.04 (±0.20) | F2 | 0.000* | G1 |
| D 14 – BASELINE | 0.04 (±0.29) | F1 | −0.02 (±0.25) | F2 | 0.020 | G2 |
| D 28 – BASELINE | −0.06 (±0.24) | F1 | 0.00 (±0.29) | F2 | 0.013 | G3 |

Conclusion: Objective Sensory (Physical Count, PUSTULES)

A Wilcoxon Signed Rank Sum Test was performed to compare the test product treated and the placebo control treated sites at baseline (thus before application of test products) and there was a statistical significant difference was found between the two test sites on a 5% level of confidence. Test product P. aliciae in a gel formulation (FCAG014/5936) tested significantly higher than the placebo gel control (FCAG014/5937).

*This is of no significance to test product efficacy

A Wilcoxon Signed Rank Sum Test was performed to determine the treatment effect by comparing the average difference values at day fourteen (D14) of the test product treated and the placebo control treated sites and there was a statistical significance difference on a 5% level of confidence. Test product FCAG014/5936 tested significantly higher than control FCAG014/5937.

A Wilcoxon Signed Rank Sum Test was performed to determine the treatment effect by comparing the average difference values at day twenty-eight (D28) of the test product treated and the placebo control treated sites and there was a statistical significance difference on a 5% level of confidence. Test product FCAG014/5936 tested significantly lower than control FCAG014/5937.

It can therefore be concluded that the product FCAG014/5936 was only effective in reducing the number of pustules; after twenty-eight (28) days of consecutive use; when compared to the placebo control FCAG014/5937.

TABLE B

Comparison of objective sensory (physical count, PAPULES) values for *P. aliciae* in a gel (FCAG014/5936) compared to the placebo gel (FCAG014/5937) test sites: Mean (±Standard Deviation)

| Time Interval | FCAG014/ 5936 | Table Ref. | FCAG014/ 5937 | Table Ref. | (Diff) p-Value | Table Ref. |
|---|---|---|---|---|---|---|
| BASELINE | 12.85 (±17.31) | F3 | 12.50 (±13.12) | F4 | *0.008 | G4 |
| D 14 − BASELINE | −2.81 (±8.67) | F3 | −2.23 (±8.07) | F4 | 0.337 | G5 |
| D 28 − BASELINE | −3.65 (±12.08) | F3 | −3.67 (±12.97) | F4 | 0.496 | G6 |

Conclusion: Objective Sensory (Physical Count, PAPULES)

A Wilcoxon Signed Rank Sum Test was performed to compare the test product treated and the placebo control treated sites at baseline (thus before application of test products) and a statistical significant difference was found between the two test sites on a 5% level of confidence. Test product FCAG014/5936 tested significantly higher than control FCAG014/5937.

*This is of no significance to test product efficacy

A t-Test was performed to determine the treatment effect by comparing the average difference values at day fourteen (D14) of the test product treated and the placebo control treated sites and there was no statistical significance difference on a 5% level of confidence. Test product FCAG014/5936 tested significantly lower than control FCAG014/5937.

A t-Test was performed to determine the treatment effect by comparing the average difference values at day twenty-eight (D28) of the test product treated and the placebo control treated sites and there was no statistical significance difference on a 5% level of confidence. Test product FCAG014/5936 tested significantly higher than control FCAG014/5937.

It can therefore not be concluded that the product FCAG014/5936 was not effective in reducing the number of papules; after twenty-eight (28) days of consecutive use twice a day; when compared to the placebo control FCAG014/5937.

TABLE 3

Comparison of objective sensory (physical count, WHITEHEADS) values for *P. aliciae* in a gel (FCAG014/5936) compared to the placebo gel (FCAG014/5937) test sites: Mean (±Standard Deviation)

| Time Interval | FCAG014/ 5936 | Table Ref. | FCAG014/ 5937 | Table Ref. | (Diff) p-Value | Table Ref. |
|---|---|---|---|---|---|---|
| BASELINE | 8.29 (±8.98) | F5 | 7.79 (±8.89) | F6 | *0.000 | G7 |
| D 14 − BASELINE | −1.88 (±7.63) | F5 | 0.85 (±6.13) | F6 | 0.007 | G8 |
| D 28 − BASELINE | −4.13 (±7.03) | F5 | −1.31 (±7.84) | F6 | <0.001 | G9 |

Conclusions: Objective Sensory (Physical Count, WHITEHEADS)

A Wilcoxon Signed Rank Sum Test was performed to compare the test product treated and the placebo control treated sites at baseline (thus before application of test products) and already a statistical significant difference was found between the two test sites on a 5% level of confidence. Test product FCAG014/5936 tested significantly higher than control FCAG014/5937.

*This is of no significance to test product efficacy

A t-Test was performed to determine the treatment effect by comparing the average difference values at day fourteen (D14) of the test product treated and the placebo control treated sites and there was a statistical significance difference on a 5% level of confidence. Test product FCAG014/5936 tested significantly lower than control FCAG014/5937.

A Wilcoxon Signed Rank Sum Test was performed to determine the treatment effect by comparing the average difference values at day twenty-eight (D28) of the test product treated and the placebo control treated sites and there was a statistical significance difference on a 5% level of confidence. Test product FCAG014/5936 tested significantly lower than control FCAG014/5937.

It can therefore be concluded that the product FCAG014/5936 was effective in reducing the number of whiteheads; after fourteen (14) to twenty-eight (28) days of consecutive use; when compared to the placebo control FCAG014/5937.

TABLE 4

Comparison of objective sensory (physical count, COMEDONES) values for *P. aliciae* in a gel (FCAG014/5936) compared to the placebo gel (FCAG014/5937) test sites: Mean (±Standard Deviation)

| Time Interval | FCAG014/ 5936 | Table Ref. | FCAG014/ 5937 | Table Ref. | (Diff) p-Value | Table Ref. |
|---|---|---|---|---|---|---|
| BASELINE | 1.19 (±1.95) | F7 | 1.08 (±1.27) | F8 | *0.000 | G10 |
| D 14 − BASELINE | −0.52 (±1.65) | F7 | −0.19 (±1.25) | F8 | <0.001 | G11 |
| D 28 − BASELINE | −0.63 (±2.00) | F7 | −0.67 (±1.21) | F8 | 0.453 | G12 |

Conclusion: Objective Sensory (Physical Count, COMEDONES)

A Wilcoxon Signed Rank Sum Test was performed to compare the test product treated and the placebo control treated sites at baseline (thus before application of test products) and already a statistical significant difference was found between the two test sites on a 5% level of confidence. Test product FCAG014/5936 tested significantly higher than control FCAG014/5937.

*This is of no significance to test product efficacy.

A Wilcoxon Signed Rank Sum Test was performed to determine the treatment effect by comparing the average difference values at day fourteen (D14) of the test product treated and the placebo control treated sites and there was a statistical significance difference on a 5% level of confidence. Test product FCAG014/5936 tested significantly lower than control FCAG014/5937.

A t-Test was performed to determine the treatment effect by comparing the average difference values at day twenty-eight (D28) of the test product treated and the placebo control treated sites and there was no statistical significance difference on a 5% level of confidence.

It can therefore be concluded that the product FCAG014/5936 was only effective in reducing the number of comedones; after fourteen (14) days of consecutive use; when compared to the placebo control FCAG014/5937.

TABLE 5

Comparison of objective sensory (physical count, BLACKHEADS) values for *P. aliciae* in a gel (FCAG014/5936) compared to the placebo gel (FCAG014/5937) test sites: Mean (±Standard Deviation)

| Time Interval | FCAG014/ 5936 | Table Ref. | FCAG014/ 5937 | Table Ref. | (Diff) p-Value | Table Ref. |
|---|---|---|---|---|---|---|
| BASELINE | 3.44 (±4.63) | F9 | 3.04 (±4.69) | F10 | *0.000 | G13 |
| D 14 − BASELINE | −0.65 (±2.74) | F9 | −0.06 (±4.73) | F10 | <0.001 | G14 |
| D 28 − BASELINE | −1.25 (±3.34) | F9 | −0.35 (+3.09) | F10 | <0.001 | G15 |

Conclusions: Objective Sensory (Physical Count, BLACKHEADS)

A Wilcoxon Signed Rank Sum Test was performed to compare the test product treated and the placebo control treated sites at baseline (thus before application of test products) and already a statistical significant difference was found between the two test sites on a 5% level of confidence. Test product FCAG014/5936 tested significantly higher than control FCAG014/5937.

*This is of no significance to test product efficacy.

A Wilcoxon Signed Rank Sum Test was performed to determine the treatment effect by comparing the average difference values at day fourteen (D14) of the test product treated and the placebo control treated sites and there was a statistical significance difference on a 5% level of confidence. Test product FCAG014/5936 tested significantly lower than control FCAG014/5937.

A Wilcoxon Signed Rank Sum Test was performed to determine the treatment effect by comparing the average difference values at day twenty-eight (D28) of the test product treated and the placebo control treated sites and there was a statistical significance difference on a 5% level of confidence. Test product FCAG014/5936 tested significantly lower than control FCAG014/5937.

It can therefore be concluded that the product FCAG014/5936 was effective in reducing the number of blackheads; after fourteen (14) twenty-eight (28) days of consecutive use; when compared to the placebo control FCAG014/5937.

TABLE 6

Comparison of objective sensory (physical count, MICROCYSTS) values for *P. aliciae* in a gel (FCAG014/5936) compared to the placebo gel (FCAG014/5937) test sites: Mean (±Standard Deviation)

| Time Interval | FCAG014/ 5936 | Table Ref. | FCAG014/ 5937 | Table Ref. | (Diff) p-Value | Table Ref. |
|---|---|---|---|---|---|---|
| BASELINE | 0.23 (±0.69) | F11 | 0.08 (±0.35) | F12 | *0.000 | G16 |
| D 14 − BASELINE | −0.10 (±0.59) | F11 | 0.00 (+0.21) | F12 | 0.010 | G17 |
| D 28 − BASELINE | −0.08 (±0.61) | F11 | −0.02 (±0.33) | F12 | 0.013 | G18 |

Conclusions: Objective Sensory (Physical Count, MICROCYSTS)

A Wilcoxon Signed Rank Sum Test was performed to compare the test product treated and the placebo control treated sites at baseline (thus before application of test products) and already a statistical significant difference was found between the two test sites on a 5% level of confidence. Test product FCAG014/5936 tested significantly higher than control FCAG014/5937.

*This is of no significance to test product efficacy.

A Wilcoxon Signed Rank Sum Test was performed to determine the treatment effect by comparing the average difference values at day fourteen (D14) of the test product treated and the placebo control treated sites and there was a statistical significance difference on a 5% level of confidence. Test product FCAG014/5936 tested significantly lower than control FCAG014/5937.

A Wilcoxon Signed Rank Sum Test was performed to determine the treatment effect by comparing the average difference values at day twenty-eight (D28) of the test product treated and the placebo control treated sites and there was a statistical significance difference on a 5% level of confidence. Test product FCAG014/5936 tested significantly lower than control FCAG014/5937.

It can therefore be concluded that the product FCAG014/5936 was effective in reducing the number of microcyst; after fourteen (14) to twenty-eight (28) days of consecutive use; when compared to the placebo control FCAG014/5937.

Plectranthus aliciae was found to be a non-irritant after 24 hours compared to the positive control sodium lauryl sulphate. Plectranthus aliciae displayed a mean visual score of 0.47 compared to the positive control of 2.01.

The results for the acne clinical studies for P. aliciae are summarised as follows:
  The active gel formulation was effective in reducing the number of pustules after twenty-eight (28) days of consecutive use when compared to the placebo control.
  The active gel formulation was effective in reducing the number of whiteheads; after fourteen (14) to twenty-eight (28) days of consecutive use when compared to the placebo control.
  The active gel formulation was effective in reducing the number of comedones after fourteen (14) days of consecutive use when compared to the placebo control.
  The active gel formulation was effective in reducing the number of blackheads after fourteen (14) twenty-eight (28) days of consecutive use when compared to the placebo control.
  The active gel formulation was effective in reducing the number of microcyst after fourteen (14) to twenty-eight (28) days of consecutive use when compared to the placebo control.

4. Conclusion

Plectranthus aliciae has not yet been identified in vitro to have antibacterial activity. In this study, P. aliciae has shown great potential for the treatment of acne vulgaris. Specifically, in antimicrobial studies, P. aliciae has shown promising microbial inhibition towards the acne causing bacteria, *C. acnes*.

Free radicals are produced during inflammatory acne. These free radicals contribute to inflammation and cause cell damage. Good antioxidant activity was observed for P. aliciae against the free radicals DPPH and NO. This could contribute in preventing inflammatory acne that could result in PIH.

Plectranthus aliciae has also shown to be non-toxic towards mouse melanocytes, human keratinocytes and was found to be non-mutagenic and can therefore be considered safe to use on skin.

The ethanolic extract of P. aliciae was active towards enzymes associated with inflammatory acne. More specifically, the inhibition of the ethanolic extract on matrix metalloproteinase-9 (MMP-9), lipase and cyclooxygenase-2 (COX-2) was confirmed in vitro.

In vivo studies confirmed that the neat ethanolic extract is a non-irritant. Acne clinical studies on a 10% gel formulation were found to be effective for various forms of acne vulgaris after fourteen to twenty-eight days of consecutive use twice a day.

In light of the foregoing, the ethanolic extract of Plectranthus aliciae has shown significant potential in the cosmetic field as an alternative, anti-acne application.

The inventor thus believes that the invention addresses the drawbacks of existing therapies for acne and PIH, by providing a novel medicament and associated therapy which is derived from nature, is organic and which reduces the negative side effects experienced by patients. The novel medicament provided is also simple and cost-effective to manufacture and the associated therapy is simple in technique.

The invention claimed is:

1. A method of preventing or treating acne comprising: topically applying a dose of Plectranthus aliciae extract, to a subject suffering from acne in the form of any one of both of acne vulgaris and juvenile, in which the acne includes any one or a combination of: comedones, whiteheads, blackheads, pustules, and microcysts.

2. The method of preventing or treating acne as claimed in claim 1, wherein the Plectranthus aliciae extract exhibits antibacterial activity against *Cutibacterium acnes*.

3. The method of preventing or treating acne, as claimed in claim 1, wherein the dose is applied at least twice daily for at least 14 consecutive days, and the dose comprises between 28 µg/ml and 1000 µg/ml Plectranthus aliciae extract.

4. The method of preventing or treating acne as claimed in claim 3, wherein the dose comprises approximately 600 µg/ml Plectranthus aliciae extract.

5. The method of preventing or treating acne as claimed in claim 1, wherein the dose is formulated in a pharmaceutical composition comprising the extract of Plectranthus aliciae and a pharmaceutically acceptable carrier selected from a cream, a lotion, a gel, an ointment, an oil, an emulsion, a serum, a skin mask, a face wash, a toner, a sunscreen, or a and foundation.

6. A pharmaceutical composition suitable for topical application for preventing or treating a skin condition in a subject in need thereof comprising:
an effective amount of Plectranthus aliciae extract;
at least one added acid, at least one added base, or a combination thereof in an amount sufficient to adjust the pH of the pharmaceutical composition to a pH of 4.5 to 5.5; and
a pharmaceutically acceptable carrier selected from a cream, a lotion, a gel, an ointment, an oil, an emulsion, a serum, a skin mask, a face wash, a toner, a sunscreen, or a foundation;
wherein the pharmaceutical composition has a pH of 4.5 to 5.5 and prevents or treats a skin condition selected from acne, post inflammatory hyperpigmentation (PIH), or a combination thereof.

7. The pharmaceutical composition as claimed in claim 6, in wherein the extract of Plectranthus aliciae is an organic solvent-based extract of Plectranthus aliciae or a water-based extract of Plectranthus aliciae.

8. The pharmaceutical composition as claimed in claim 7, wherein the organic solvent-based extract is an ethanol-based extract.

9. The pharmaceutical composition as claimed in claim 6, wherein the pharmaceutical composition comprises at least 28 µg/ml Plectranthus aliciae extract.

10. The pharmaceutical composition as claimed in claim 6, wherein the pharmaceutical composition comprises approximately 600 µg/ml Plectranthus aliciae extract.

11. The pharmaceutical composition as claimed in claim 6, wherein the pharmaceutical composition comprises one or more of: a preservative, a surfactant, a gelling agent, a thickening agent, an antioxidant, an emulsifier, an emollient, a solubilizer, a humectant, a stabilizer, a chelating agent, and a buffer.

12. The pharmaceutical composition as claimed in claim 6, wherein the skin condition is acne and the pharmaceutical composition exhibits antibacterial activity towards *Cutibacterium acnes*.

13. The pharmaceutical composition as claimed in claim 6, wherein the pharmaceutical composition comprises at least 28 µg/ml Plectranthus aliciae.

14. The pharmaceutical composition as claimed in claim 6, wherein the pharmaceutical composition comprises at least one bioactive compound originating from the extract of Plectranthus aliciae, wherein the at least one bioactive compound is luteolin in an amount of at least 62.5 µg/ml of the pharmaceutical composition.

15. The pharmaceutical composition as claimed in claim 6, wherein the pharmaceutical composition comprises an added preservative.

16. A pharmaceutical gel composition suitable for topical application comprising:
an extract of Plectranthus aliciae;
at least one chelating agent;
at least one thickening agent;
at least one humectant;
at least one additional additive; and
at least one acid, at least one base, or a combination thereof in an amount sufficient to adjust the pH of the pharmaceutical composition to a pH of 4.5 to 5.5; and water;
wherein the pharmaceutical gel composition is effective for preventing or treating a skin condition selected from acne, post inflammatory hyperpigmentation (PIH), or a combination thereof.

17. The pharmaceutical gel composition as claimed in claim 16, wherein the extract of Plectranthus aliciae is an organic-solvent-based extract or a water-based extract.

18. The pharmaceutical gel composition as claimed in claim 17, wherein the organic-solvent-based extract is in the form of an ethanolic extract.

19. The pharmaceutical gel composition as claimed in claim 18 comprising approximately 10% concentration of ethanolic extract of Plectranthus aliciae.

20. The pharmaceutical gel composition as claimed in claim 16, wherein:
the at least one chelating agent is tetrasodium EDTA,
the at least one humectant is propylene glycol,
the at least one thickening agent is a carbomer,
the at least one acid, the at least one base, or the combination thereof is sodium hydroxide (NaOH),
and the at least one additional additive is diazolidinyl urea, methylparaben, and propylparaben.

* * * * *